United States Patent
Olivier-Bourbigou et al.

(10) Patent No.: US 6,667,269 B2
(45) Date of Patent: Dec. 23, 2003

(54) CATALYTIC COMPOSITION AND PROCESS FOR DIMERIZATION, CODIMERIZATION AND OLIGOMERIZATION OF OLEFINS

(75) Inventors: Helene Olivier-Bourbigou, Rueil Malmaison (FR); Dominique Commereuc, Meudon (FR); Stephane Harry, Montesson (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/815,332

(22) Filed: Mar. 23, 2001

(65) Prior Publication Data

US 2001/0047121 A1 Nov. 29, 2001

(30) Foreign Application Priority Data

Mar. 23, 2000 (FR) .............................................. 00 03820

(51) Int. Cl.[7] .......................... B01J 31/00; B01J 37/00; C08F 4/02; C08F 4/60; C07C 2/24
(52) U.S. Cl. ..................... 502/117; 502/167; 585/513; 585/527; 585/531
(58) Field of Search .................... 502/117, 167; 585/513, 527, 531

(56) References Cited

U.S. PATENT DOCUMENTS

| | | | |
|---|---|---|---|
| 5,166,114 A | 11/1992 | An-hsiang | 502/117 |
| 5,324,799 A | 6/1994 | Yano et al. | 526/139 |
| 5,728,839 A * | 3/1998 | Herrmann et al. | 548/103 |
| 6,313,331 B1 * | 11/2001 | Cavell et al. | 502/117 |
| 6,060,568 A1 * | 5/2002 | Cavell et al. | 502/117 |
| 6,433,113 B1 * | 8/2002 | Mukerjee et al. | 502/117 |
| 6,576,724 B2 * | 6/2003 | Olivier-Bourbigou et al. | 502/167 |
| 2001/0049398 A1 * | 12/2001 | Olivier-Bourbigou et al. | 502/162 |
| 2002/0107138 A1 * | 8/2002 | Hoveyda et al. | 502/167 |
| 2003/0023123 A1 * | 1/2003 | Paulson et al. | 585/527 |

FOREIGN PATENT DOCUMENTS

| | | |
|---|---|---|
| DE | 44 47 066 A1 | 7/1996 |
| EP | 0 646 412 A1 * | 4/1995 |
| EP | 0798 041 A1 | 10/1997 |

OTHER PUBLICATIONS

Grant and Hackh's Chemical Dictionary, 5th ed., no publication date given, pp. 87, 438.*

* cited by examiner

*Primary Examiner*—Mark L. Bell
*Assistant Examiner*—J. Pasterczyk
(74) *Attorney, Agent, or Firm*—Millen, White, Zelano & Branigan, P.C.

(57) ABSTRACT

A catalytic composition for the dimerization, the codimerization or the oligomerization of olefins is obtained by bringing into contact at least one nickel compound that contains a heterocyclic carbene with at least one hydrocarbylaluminum halide and optionally at least one organic solvent. It is used in a process of dimerization, codimerization or oligomerization of olefins.

38 Claims, No Drawings

CATALYTIC COMPOSITION AND PROCESS FOR DIMERIZATION, CODIMERIZATION AND OLIGOMERIZATION OF OLEFINS

CROSS-REFERENCE TO RELATED APPLICATION

This application is related to our concurrently filed application entitled "Catalytic Composition And Process For The Catalysis Of Dimerization, Codimerization And Oligomerization Of Olefins", Ser. No. 09/815,347, filed Mar. 23, 2001 based on French Priority Application No. 00/03.819, filed Mar. 23, 2000.

FIELD OF THE INVENTION

This invention relates to the catalytic dimerization, codimerization and oligomerization of olefins.

It has as its object a catalytic formula that results from the dissolution of a nickel complex that contains at least one heterocyclic carbene ligand with at least one hydrocarbylaluminum halide and optionally at least one organic solvent. This invention also has as its object the use of this catalytic composition in processes of dimerization, codimerization and/or oligomerization of olefins.

BACKGROUND OF THE INVENTION

It is known to prepare catalysts for dimerization or codimerization of monoolefins such as ethylene, propylene, butenes or pentenes. Among these catalysts, it is possible to cite in particular by way of examples: the products for interaction of π-allyl nickel phosphine halides with Lewis acids (French Patent FR-B-1 410 430), the products for interaction of nickel phosphine halides with Lewis acids (U.S. Pat. No. 3,485,881) and the products for interaction of certain nickel carboxylates with hydrocarbylaluminum halides (U.S. Pat. No. 3,321,546).

Nearly all of these catalysts use a ligand such as an organic phosphorus compound. It is preferable, however, to be able to use phosphorus-free oligomerization catalysts. It would be possible to use catalysts in which nickel is deposited on a mineral substrate that comprises acid sites, such as silica, alumina or silica-aluminas. These are solid catalysts, however, unlike catalysts in the liquid phase of the invention.

Some organometallic nickel complexes that contain heterocyclic carbene ligands have been described in the prior art (International Application WO-A-99/06 004, U.S. Pat. No. 5,728, 839 and Patent Application EP-A-0 798 041). Such complexes have the advantage of being very stable. More particularly, these monocarbene or bicarbene ligands lead to nickel complexes that are thermally and chemically stable primarily with regard to oxidation. These carbene ligands were the object of a survey in Angew. Chem. Int. Ed. Engl. 1997, 36, 2162. These are σ-donor ligands and π-acceptor ligands that form very stable bonds with transition metals. Their electronic properties can be compared to those of basic trialkylphosphines.

SUMMARY OF THE INVENTION

It has now been found that bringing into contact
a nickel complex that carries at least one monocarbene or bicarbene ligand that corresponds to, for example, Formulas (I) and (II) that are provided below;
with at least one hydrocarbylaluminum halide;
and optionally an organic solvent led to an active system for dimerization, codimerization and/or oligomerization of olefins.

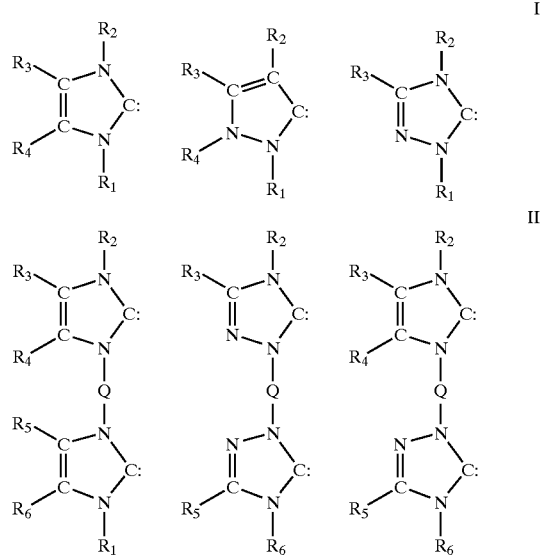

DETAILED DESCRIPTION OF THE INVENTION

The nickel compounds that are used according to the invention are salts of nickel or organometallic compounds that may or may not be charged and that correspond to the general formula (already described in Patent Application EP-A-0 798 041):

$$(Ni_aX_bY_dL_c)^n(A)_n$$

in which:
a, b, c, d and n are integers with a equal to 1, 2 or 3; b equal to 0 to 2×a; d equal to 0 to 2×a; c equal to 1 to 4×b; n equal to 0, 1 or 2;

X and Y, identical or different, each represent a mono- or poly-dentate ligand that may or may not be charged; by way of examples, it is possible to cite halides, carboxylates (for example ethyl-2-hexanoate), acetylacetonate, sulfate, phenolates, mono- and di-olefins, π-aromatic compounds, alkyl or aryl radicals, phosphines, phosphates and carbon monoxide;

L is a heterocyclic mono- or di-carbene that corresponds to, for example, one of general formulas (I) and (II) above, in which $R_1$, $R_2$, $R_3$, R4, $R_5$ and $R_6$, identical or different, each represent hydrogen, a hydrocarbon-containing group, aliphatic group, saturated or unsaturated group, or aromatic group that comprises 1 to 12 carbon atoms, and Q represents an aliphatic divalent radical with 1 to 4 carbon atoms;

A is a sparingly coordinating anion; by way of examples, it is possible to cite tetrafluoroborate anions, hexafluorophosphate anions, tetraphenylborate anions and derivatives thereof, tetrachloroaluminate anions, hexafluoroantimonate anions, trifluoroacetate anions, trifluoromethylsulfonate anions and acetate anions.

Heterocyclic carbenes L can be generated from corresponding imidazolium or bis(azolium) salts by deprotonation. The transition metal can play the role of reducing agent.

By way of nonlimiting examples of heterocyclic mono- or bicarbene ligands, the carbene ligands that are described by formulas (1), (2) and (3) that are given below will be cited.

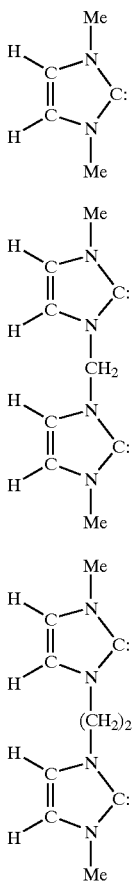

By way of nonlimiting examples of nickel compounds that can be used according to the invention, it is possible to cite the complexes of NiCl$_2$, [dimethyl-1,3-imidazolylidene-2]$_2$; NiI$_2$, [dimethyl-1,3-imidazolylidene-2]$_2$; π-allyl nickel chloride (dimethyl-1,3-imidazolylidene-2) ; NiCl$_2$, [dimethyl-1,1'-imidazole-diylidene-2,2'-methylene-3,3']$_2$ and NiCl$_2$, [dimethyl-1,1'-imidazole-diylidene-2,2'-ethylene-3,3']$_2$, NiI$_2$[dimethyl-1,1'-imidazole-diylidene-2,2'-methylene-3,3']$_2$ and NiI$_2$, [dimethyl-1,1'-imidazole-diylidene-2,2'-ethylene-3,3']$_2$.

The hydrocarbylaluminum halide derivatives that are used according to the invention have as a general formula AlR$_x$X$_{3-x}$, in which R is a hydrocarbon-containing radical comprising 1 to 12 carbon atoms, which can be alkyl, linear or branched, cycloalkyl, aryl or aralkyl, whereby X is chlorine or bromine and x is a number from 1 to 3. By way of nonlimiting examples of these derivatives, it is possible to cite isobutylaluminum sesquichloride, ethylaluminum sesquichloride, dichloroisobutylaluminum, dichloroethylaluminum and chlorodiethylaluminum.

The components of the catalytic formula can be mixed in any order.

The optional solvent that makes it possible to carry out the mixing of the components of the catalytic formula and in which the catalysis can be carried out is a hydrocarbon-containing solvent, for example an alkane or an aromatic hydrocarbon, or else a halogenated hydrocarbon or else the mixture of olefins that is produced in the oligomerization reaction.

The molar ratio of the organic aluminum compound to the nickel compound, expressed by the Al/Ni ratio, is, for example, from 2/1 to 50/1 and preferably 2/1 to 20/1.

The olefins that can be dimerized, codimerized or oligomerized by the catalytic compositions according to the invention are ethylene, propylene, n-butenes and n-pentenes, alone or in a mixture, pure or diluted by one or more alkane(s), such as are found in "fractions" that are obtained from petroleum refining processes, such as catalytic cracking or steam-cracking.

The catalytic reaction of dimerization, oligomerization or codimerization of olefins, which is also an object of the invention, can be conducted in a closed system, in a semi-open system or continuously with one or more reaction stages. The reaction temperature can be −40 to +80° C., preferably −20 to +50° C., under pressure conditions such that the reagents are kept at least for the most part in liquid phase or condensed phase. The heat that is produced by the reaction can be eliminated by all of the means that are known to one skilled in the art.

The process can be used in a reactor with one or more reaction stages in series, whereby the preconditioned olefinic feedstock and/or the catalytic composition is introduced continuously or in the first stage or in the first and any other of the stages. At the outlet of the reactor, the catalyst can be deactivated, for example by injection of ammonia and/or an aqueous solution of soda and/or an aqueous solution of sulfuric acid. The unconverted olefins and the alkanes that are optionally present in the feedstock are then separated from the oligomers by distillation.

The products of this process can find an application, for example, as components of fuels for automobiles and/or as feedstocks in a hydroformylation process for the synthesis of aldehydes and alcohols.

The following examples illustrate the invention without limiting its scope.

EXAMPLE 1

Preparation of the Nickel Complex NiCl$_2$, [Dimethyl-1,3-imidazolylidene-2]$_2$:

The nickel complex is prepared by an improvement of the synthesis that is described in Organometallics, 1997, 16, 2209.

In a Schlenk tube, pre-dried nickel acetate (6 mmol) is vigorously stirred with dimethyl-1,3-imidazolium iodide (12 mmol) in nitromethane (60 mL). It is heated to 150° C. by putting the pump under vacuum for an hour. It is allowed to cool, then the red complex that is formed with hot tetrahydrofuran (500 mL) is extracted. The tetrahydrofuran is then evaporated under a vacuum, and the red compound is washed with diethyl ether (140 mL). A second washing with absolute ethanol (15 mL) is necessary to eliminate the dimethyl-1,3-imidazolium iodide that has not reacted.

EXAMPLE 2

Dimerization of Butene

A 100 mL glass reactor that is equipped with a probe for measuring temperature, a small magnetized bar to ensure good stirring and a double jacket that allows the circulation of a cooling liquid was purged of air and moisture and kept at the atmospheric pressure of butene-1. 50.2 mg (0.1 mmol) of the complex NiI$_2$, [dimethyl-1,3-imidazolylidene-2]$_2$ and 10 mL of heptane are introduced therein, then the temperature was lowered to 10° C. and 1.5 mmol of dichloroethylaluminum dissolved in 2 mL of heptane was injected with a syringe. Stirring was started, and absorption of butene was observed immediately. When the reactor was three quarters full of liquid (at the end of half an hour), stirring was stopped. At this time, a total of 24 g of butene had been introduced. 4 kg of products per gram of Ni was produced over half an hour. These products consist of 90% by weight of dimers (determination by chromatography in gaseous phase).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 00/03.820, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyst composition obtained from a process comprising contacting:

at least one nickel complex that carries at least one heterocyclic carbene ligand L;
   with at least one hydrocarbylaluminum halide;
   and optionally with an organic solvent.

2. A catalyst composition according to claim 1, in which the nickel complex corresponds to general formula $(Ni_aX_bY_dL_c^n(A)_n)$, in which a, b, c, d and n are integers with a equal to 1, 2 or 3; b equal to 0 or 1 to 2 times a;
   d equal to 0 or 1 to 2 times a; c equal to 1 times to up to 4 times b; and n equal to 0, 1 or 2; with the proviso that (b+d+a) is greater than zero,
   X and Y, identical or different, each represent an optionally charged monodentate or polydentate ligand;
   L is a heterocyclic mono- or bi-carbene;
   A is a weakly coordinating anion.

3. A catalyst composition according to claim 2 wherein ligand L corresponds to one of formulas (I) or (II):

Type I

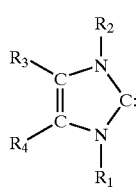 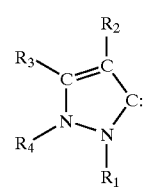 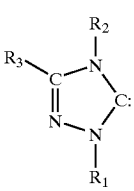

Type II

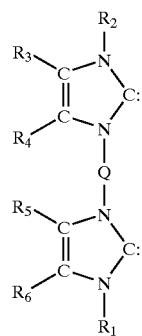 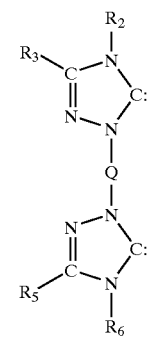 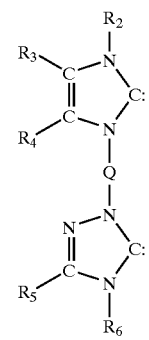

in which $R_1$, $R_2$, $R_3$, $F_4$, $R_5$ and $R_6$, identical or different, each represent hydrogen, a hydrocarbon-containing group, an aliphatic group, a saturated or unsaturated group, or an aromatic group, comprising 1 to 12 carbon atoms and Q represents an aliphatic bivalent radical with 1 to 4 carbon atoms.

4. A catalyst composition according to claim 1, wherein L corresponds to at least one of formulas (1), (2) and (3)

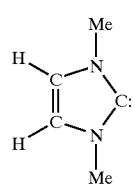

(1)

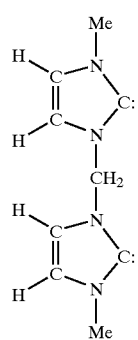

(2)

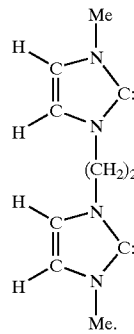

(3)

5. A catalyst composition according to claim 2, wherein at least one of b and d is not zero and X and Y represent at least one of a halide, a carboxylate, acetylacetonate, sulfate, a phenate, a mono- and di-olefin, a π-aromatic compound, an alkyl or aryl radical, a phosphine, a phosphite or carbon monoxide.

6. A catalyst composition according to claim 2, wherein n is not zero and A represents at least one anion selected from the group consisting of trifluoromethylacetate, trifluoromethylsulfonate and acetate.

7. A catalyst composition according to claim 2, wherein the nickel complex is $NiCl_2$[dimethyl-1,3-imidazolylidene-2]$_2$;

$NiI_2$[dimethyl-1,3-imidazolylidene-2]$_2$;

π-allyl nickel chloride (dimethyl-1,3-imidazolylidene-2);

$NiCl_2$[dimethyl-1,1'-imidazole-diylidene-2,2'-methylene-3,3']$_2$;

$NiCl_2$[dimethyl-1,1'-imidazole-diylidene-2,2'-ethylene-3,3']$_2$;

$NiI_2$[dimethyl-1,1-imidazole-diylidene-2,2'-methylene-3,3']$_2$; or $NiI_2$[dimethyl-1,1-imidazole-diylidene-2,2'-ethylene-3,3']$_2$.

8. A catalyst composition according to claim 1, wherein the hydrocarbyl aluminum halide corresponds to general formula $AlR_{X3-X}$, in which R is a hydrocarbon-containing radical, X is chlorine or bromine and x is a number in the range of 1 to less than 3.

9. A catalyst composition according to claim 8, wherein the hydrocarbylaluminum halide is isobutylaluminum sesquichloride, ethylaluminum sesquichloride, dichloroisobutylaluminum, dichloroethylaluminum or chlorodiethylaluminum.

10. A catalyst composition according to claim 1, having a ratio of the hydrocarbyl aluminum halide to the nickel complex, expressed by the Al/Ni ratio, of 2/1 to 50/1.

11. A catalyst composition according to claim 1, wherein said contacting is conducted with said organic solvent, and said organic solvent comprises at least one of an alkane, an aromatic hydrocarbon, a halogenated hydrocarbon and an olefin produced by dimerization, codimerization or oligomerization.

12. A process of dimerization, codimerization or oligomerization of at least one olefin, comprising contacting said olefin with a catalyst composition according to claim 1.

13. A process according to claim 12, wherein the reaction of dimerization, codimerization or oligomerization of the olefin(s) is conducted in a closed system, semi-open system or continuously, with one or more reaction stages, while being stirred and at a temperature of −40 to +80° C.

14. A process according to claim 12, wherein the olefin(s) is (are) selected from the group consisting of ethylene, propylene, n-butenes, n-pentenes, and mixtures thereof optionally diluted by at least one alkane.

15. A process according to claim 12, wherein the olefin(s) is (are) contained in a fraction obtained from a petroleum refining process.

16. A catalyst composition according to claim 8, wherein R is alkyl, cycloalkyl, aryl or aralkyl.

17. A catalyst composition according to claim 7, wherein the hydrocarbylaluminum halide is isobutylaluminum sesquichloride, ethylaluminum sesquichloride, dichloroisobutylaluminum, dichloroethylaluminum or chlorodiethylaluminum.

18. A process of dimerization, codimerization or oligomerization of at least one olefin, comprising contacting said olefin with a catalyst composition according to claim 17.

19. A catalyst composition obtained from a process comprising contacting:

at least one nickel complex that carries at least one heterocyclic carbene ligand L with at least one hydrocarbylaluminum halide;

and wherein the nickel complex corresponds to general formula $(Ni_aX_bY_dL_c)^n(A)_n$, in which a, b, c, d and n are integers with a equal to 1, 2 or 3; b equal to 0 to up to 2 times a; d equal to 0 to up to 2 times a; c equal to 1 to up to 4 times b; and n equal to 0, 1 or 2;

X and Y, identical or different, each represent an optionally charged monodentate or polydentate ligand;

L is a heterocyclic mono- or di-carbene;

A is selected from the group consisting of tetrafluoroborate, hexafluorophosphate, a tetraphenylborate, a tetrachloroaluminate, and hexafluoroantimonate.

20. A catalyst composition according to claim 19, wherein at least one of b and c is not zero and X and Y represent at least one of a halide, a carboxylate, acetylacetonate, sulfate, a phenolate, a mono- and di-olefin, a π-aromatic compound, an alkyl or aryl radical, a phosphine, a phosphite or carbon monoxide.

21. A catalyst composition according to claim 19, wherein n is not zero and A represents at least one anion selected from the group consisting of trifluoromethylacetate, trifluoromethylsulfonate and acetate.

22. A catalyst composition according to claim 19, wherein the nickel complex is $NiCl_2$[dimethyl-1,3-imidazolylidene-2]$_2$;

$NiI_2$[dimethyl-1,3-imidazolylidene-2]$_2$;

π-allyl nickel chloride (dimethyl-1,3-imidazolylidene-2);

$NiCl_2$[dimethyl-1,1'-imidazole-diylidene-2,2'-methylene-3,3']$_2$;

$NiCl_2$[dimethyl-1,1'-imidazole-diylidene-2,2'-ethylene-3,3']$_2$;

$NiI_2$[dimethyl-1,1-imidazole-diylidene-2,2'-methylene-3,3']$_2$; or $NiI_2$[dimethyl-1,1-imidazole-diylidene-2,2'-ethylene-3,3']$_2$.

23. A catalyst composition according to claim 1, wherein cyclic atoms of said ligand consist of carbon and nitrogen.

24. A process of dimerization, codimerization or oligomerization of at least one olefin, comprising contacting said olefin with a catalyst composition according to claim 12.

25. A process of dimerization, codimerization or oligomerization of at least one olefin, comprising contacting said olefin with a catalyst composition according to claim 3.

26. A process of dimerization, codimerization or oligomerization of at least one olefin, comprising contacting said olefin with a catalyst composition according to claim 4.

27. A process of dimerization, codimerization or oligomerization of at least one olefin, comprising contacting said olefin with a catalyst composition according to claim 5.

28. A process of dimerization, codimerization or oligomerization of at least one olefin, comprising contacting said olefin with a catalyst composition according to claim 6.

29. A process of dimerization, codimerization or oligomerization of at least one olefin, comprising contacting said olefin with a catalyst composition according to claim 3.

30. A process of dimerization, codimerization or oligomerization of at least one olefin, comprising contacting said olefin with a catalyst composition according to claims 8.

31. A process of dimerization, codimerization or oligomerization of at least one olefin, comprising contacting said olefin with a catalyst composition according to claim 9.

32. A process of dimerization, codimerization or oligomerization of at least one olefin, comprising contacting said olefin with a catalyst composition according to claim 10.

33. A process of dimerization, codimerization or oligomerization of at least one olefin, comprising contacting said olefin with a catalyst composition according to claim 11.

34. A process of dimerization, codimerization or oligomerization of at least one olefin, comprising contacting said olefin with a catalyst composition according to claim 19.

35. A process of dimerization, codimerization or oligomerization of at least one olefin, comprising contacting said olefin with a catalyst composition according to claim 20.

36. A process of dimerization, codimerization or oligomerization of at least one olefin, comprising contacting said olefin with a catalyst composition according to claim 21.

37. A process of dimerization, codimerization or oligomerization of at least olefin, contacting said olefin with a catalyst composition according to claim 22.

38. A process of dimerization, codimerization or oligomerization of at least one olefin, contacting said olefin with a catalyst composition according to claim 23.

* * * * *

UNITED STATES PATENT AND TRADEMARK OFFICE
CERTIFICATE OF CORRECTION

PATENT NO. : 6,667,269 B2
DATED : December 23, 2003
INVENTOR(S) : Helene Olivier-Bourbigou et al.

It is certified that error appears in the above-identified patent and that said Letters Patent is hereby corrected as shown below:

Column 8,
Line 46, reads "claim 12" should read -- claim 2 --
Line 61, reads "claim 3" should read -- claim 7 --

Signed and Sealed this

Fourteenth Day of September, 2004

JON W. DUDAS
*Director of the United States Patent and Trademark Office*